United States Patent
Gagnieux et al.

(10) Patent No.: US 10,350,347 B2
(45) Date of Patent: Jul. 16, 2019

(54) TRAY FOR POSITIONING ELONGATED OBJECTS, IN PARTICULAR SYRINGE BODIES OR SYRINGES

(71) Applicant: Becton Dickinson France, Le Pont de Claix (FR)

(72) Inventors: Samuel Gagnieux, Echirolles (FR); Thomas Dubois, Echirolles (FR); Franck Carrel, Saint Jean de Vaulx (FR); Nicolas Eon, Grenoble (FR); Aurelie Allanic, Le Cheylas (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 16/173,479

(22) Filed: Oct. 29, 2018

(65) Prior Publication Data

US 2019/0060559 A1 Feb. 28, 2019

Related U.S. Application Data

(63) Continuation of application No. 15/882,167, filed on Jan. 29, 2018, now Pat. No. 10,143,793, which is a
(Continued)

(51) Int. Cl.
*B65D 85/20* (2006.01)
*A61M 5/00* (2006.01)
(Continued)

(52) U.S. Cl.
CPC .......... *A61M 5/008* (2013.01); *B65D 25/108* (2013.01); *B01L 9/54* (2013.01); *B01L 2200/025* (2013.01)

(58) Field of Classification Search
CPC ........ B65D 25/108; A61M 5/008; B01L 9/54; B01L 9/543; B01L 2200/025
(Continued)

(56) References Cited

U.S. PATENT DOCUMENTS 4,154,795 A * 5/1979 Thorne ................. B01L 3/5085
206/460
RE34,133 E * 11/1992 Thorne ................. B01L 3/5085
206/460
(Continued)

FOREIGN PATENT DOCUMENTS

EP 1449551 A1 8/2004

*Primary Examiner* — Luan K Bui
(74) *Attorney, Agent, or Firm* — The Webb Law Firm

(57) ABSTRACT

This tray includes spaced apart openings arranged in parallel rows, intended to receive the bodies of the elongated objects, and projections making it possible to place the flanges of the elongated objects inserted in these openings in a determined angular position on the tray when the bodies of these elongated objects are engaged in these openings. According to the invention: said projections are arranged so as to place the length of said flanges in a determined angular position with respect to the rows of openings, and the openings of a first row of openings are arranged with respect to a second row of openings adjacent to said first row, such that after installation of the elongated objects on the tray, the flanges of the objects inserted in the openings of said the first row imbricates with the flanges of the objects inserted in the openings of said second row, i.e. each flange of an object of said the first row is positioned in a space existing between the two adjacent flanges of the objects of said second row, in the immediate vicinity of these two flanges.

12 Claims, 4 Drawing Sheets

Related U.S. Application Data continuation of application No. 13/389,111, filed as application No. PCT/IB2009/006907 on Aug. 7, 2009, now abandoned.

(51) Int. Cl.
  *B65D 25/10* (2006.01)
  *B01L 9/00* (2006.01)

(58) Field of Classification Search
  USPC ....... 206/443, 480, 486, 488, 490, 499, 557, 206/560, 562, 563, 565; 211/74, 85.18, 211/85.29; 248/309.1, 311.2, 311.3, 314
  See application file for complete search history.

(56) References Cited

U.S. PATENT DOCUMENTS

| | | | |
|---|---|---|---|
| 5,667,495 A | 9/1997 | Bitdinger et al. | |
| 6,098,803 A * | 8/2000 | Tanaka | B65D 19/16 206/386 |
| 6,286,678 B1 * | 9/2001 | Petrek | B01L 9/543 206/443 |
| 6,719,141 B2 * | 4/2004 | Heinz | A61M 5/008 206/443 |
| 6,722,054 B2 * | 4/2004 | Yarborough | F26B 5/06 34/284 |
| 6,872,423 B2 * | 3/2005 | Brown | A63B 45/00 118/500 |
| 6,907,679 B2 * | 6/2005 | Yarborough | A61M 5/002 34/237 |
| 7,100,768 B2 | 9/2006 | Grimard et al. | |
| 7,232,038 B2 * | 6/2007 | Whitney | B01L 9/06 211/74 |
| 7,428,807 B2 | 9/2008 | Vander Bush et al. | |
| 8,100,263 B2 | 1/2012 | Vanderbush et al. | |
| 8,485,357 B2 * | 7/2013 | Song | A61M 5/002 206/366 |
| 2009/0100802 A1 * | 4/2009 | Bush | A61M 5/002 53/434 |
| 2010/0012546 A1 * | 1/2010 | Togashi | A61M 5/008 206/534.1 |

* cited by examiner

TRAY FOR POSITIONING ELONGATED OBJECTS, IN PARTICULAR SYRINGE BODIES OR SYRINGES

CROSS REFERENCE TO RELATED APPLICATIONS

This application is a continuation of U.S. application Ser. No. 15/882,167, filed Jan. 29, 2018, which is a continuation of U.S. application Ser. No. 13/389,111, filed Apr. 20, 2012, which is a United States national phase application of International Application No. PCT/IB2009/006907, filed Aug. 7, 2009, the entire disclosures of each of which are hereby incorporated by reference.

The present invention relates to a tray for positioning elongated objects, in particular syringe bodies or syringes. Each one of these elongated objects comprises a body, notably cylindrical, and a noncircular flange, having a length greater than its width. In the case of a syringe body, the flange is located at one end of the cylindrical body, or near this end. The flange can be integral with the syringe body or can be formed by a separate part mounted on the proximal end of this body.

It is frequent that syringe bodies or syringes are to be transported from one site to another site, either when they are manufactured on a site and are filled on another site, or, less frequently, when they are manufactured and filled on the same site and are to be used on another site.

For this transport, it is current to group the syringe bodies or syringes on a tray having openings and tubular walls or chimneys coaxially surrounding these openings, the openings receiving the syringe bodies and the flanges bearing against said tubular walls or chimneys. The tray with the syringe bodies or syringes thereon is placed in a packaging box, which is sealed and sterilized. At destination, the box is opened and the tray is extracted therefrom, the tray being subsequently used for handling and/or filling of the syringe bodies or syringes by automated means.

A known tray for grouping syringe bodies or syringes includes a plate and a plurality of chimneys projecting from at least a face of this plate, these chimneys being dimensioned to receive the syringe bodies or syringes through them until the flanges of the syringe bodies or syringes bear against the upper free edges of these chimneys.

With this tray, however, the number of syringe bodies or syringes that can be installed on a same tray is limited. This limitation has a direct consequence on the number of packaging boxes having to be used to transport a given number of syringe bodies or syringes and thus on the cost of the packaging and of the transport of these syringe bodies or syringes. For the user, it is necessary to open and handle a significant number of packaging boxes to process a given number of syringe bodies or syringes.

In order to increase the density of syringes in a tray, and thus minimizing the handling operations, it would be useful for instance to have the rows of syringes closer one to another; however, due to the particular shape of the syringe flanges, it is not possible, with conventional trays, to have syringe rows closer because flanges might then contact and there is a high risk of breakage during handling operations.

It is besides known by the document EP 1 449 551 A1 to provide the plate of the tray with projecting walls forming rectangular housings for receiving the flanges of the syringe bodies. These housings orient these flanges in a determined position on the tray, in which the length and the width of the flanges are perpendicular to the rows and the rows of syringe bodies on the tray.

The tray according to this patent application does not overcome the above-mentioned drawback, notably because the geometry of the rectangular housings leads to additional handling operations for clipping and unclipping the syringe flanges.

The object of the present invention is to overcome this drawback.

The tray concerned includes, in a known way, a plate with spaced apart openings arranged in parallel rows, intended to receive the bodies of the elongated objects, and projections that place the flanges of the elongated objects inserted in these openings in a determined position on the tray when said bodies of these elongated objects are engaged in these openings.

According to the invention, said projections are arranged so as to place the length of said flanges in a determined angular position with respect to the rows of openings, and the openings of a first row of openings are arranged with respect to a second row of openings adjacent to said first row, such that after installation of the elongated objects on the tray, the flanges of the objects inserted in the openings of said the first row imbricates with the flanges of the objects inserted in the openings of said second row.

By "determined angular position", it must be understood that the lengths of the flanges are neither parallel nor perpendicular to the longitudinal directions of the rows of openings.

By "imbricates", it must be understood that each flange of an object of said first row is positioned in a space existing between the two adjacent flanges of the objects of said second row, in the immediate vicinity of these two flanges.

The tray according to the invention thus makes it possible to position the flanges of the elongated objects according to given angular orientations, identical from one row to an adjacent row, and thus to put these flanges in the immediate vicinity one with each other, with imbrications. The openings can thus be arranged in positions notably closer than the openings of a tray according to the prior art, and the density of these objects on this tray can be significantly increased, while allowing the external dimensions of the tray to remain identical to those of the existing trays. This conservation of these external dimensions is indeed necessary not to induce too important modifications of the automated treatment units of the elongated objects, in particular of the units for handling and/or filling syringe bodies.

This increase in the density of the number of elongated objects makes it possible to reduce the number of packagings that are necessary for the conditioning and the transport of a given number of these objects, and thus to reduce the costs of conditioning and transporting these objects. The subsequent operations of opening and handling the boxes containing these objects are also reduced accordingly.

Said projections of the tray can have any appropriate shape making it possible to maintain the flanges in said angular position when the elongated objects are in place in the openings of the tray. According to a preferred embodiment of the invention, each projection includes a cylindrical stem and a radial wall, extending radially from this cylindrical stem, said cylindrical stem being arranged substantially between two openings of the same row of openings so that the flanges of the elongated objects engaged in these openings come in its immediate vicinity, as well as the flange of an elongated object engaged in the contiguous opening of the adjacent row, and said radial wall being arranged according to the desired determined angular position of the flanges of the elongated objects and being intended to be inserted between the flanges of the elongated objects inserted in two contiguous openings of two rows of adjacent openings.

Said projections can also be in the form of rectilinear walls, or of studs having a form corresponding to that of spaces existing between the flanges of two adjacent rows of objects.

Said projections can be arranged so that the flanges come in contact therewith or come in the immediate vicinity therewith when the objects are in a complete engagement in the openings of the tray, these projections thus allowing maintaining the flanges in said determined angular position.

These projections thus only make it possible to maintain the flanges in said determined angular position. The orientation of these flanges necessary for their engagement near the projections or in the immediate vicinity of these projections is then carried out by adequate angular positioning of the objects at the moment of their installation on the tray, this positioning being operated manually or mechanically.

According to another possibility, said projections include sloped edges forming ramps which the flanges are intended to meet during the engagement of the objects in the openings of the tray and against which these flanges slip further to this meeting, this slip allowing bringing the flanges in said determined angular position.

The elongated objects can thus be inserted in the openings of the tray according to an unspecified angular position of their flanges, these objects being brought in said determined angular position by the slip of the flanges against said projections. This slip can be carried out by itself or be caused for example by a vibration transmitted to the tray.

Preferably, in this case, the tray includes projections arranged on two diametrically opposed sides of the openings, and the two projections of a same opening include edges of reversed slopes from one projection to the other of this same opening.

Said sloped edges of the projections can be rectilinear or exhibit a curved form.

The projections can also exhibit bevelled free edges, i.e. sloped in the direction of the thickness of these projections, which the flanges are intended to meet during the engagement of the objects in the openings of the tray and against which these flanges slip further to this meeting.

This slip makes it possible to bring the flanges in said determined angular position or contributes to bring these flanges in this position.

The projections can be interrupted from a row of openings to an adjacent row of openings, or can be continuous from a row of openings to an adjacent row of openings.

The tray can include no chimneys, in which case said projections are fixed to the plate of this tray; when the tray includes chimneys delimiting said openings for receiving the elongated objects, said projections can be arranged on the level of the free edges of these chimneys.

Said projections can include retention means making it possible to carry out retention of the flanges, in particular by clamping or snapping.

The packaging box containing the tray can thus be turned upside down without risk of the flanges coming out of said projections, and thus without loss of said predetermined angular position.

The tray can also include, with a same aim, chimneys delimiting said openings for receiving said elongated objects, these chimneys having lengths such that the flanges of the elongated objects received therein are, after installation of the tray in a packaging box and installation on the box of a membrane immobilized with respect to the box, located in the immediate vicinity of this membrane.

The tray can also include, still with a same aim, a heightening base part making it possible to heighten the plate of the tray with respect to a shoulder for supporting this tray arranged in said packaging box, this base part making it possible to raise the tray so that the flanges of the elongated objects placed on the tray are located in the immediate vicinity of a membrane immobilized with respect to the box.

The invention will be readily understood, and other features and advantages thereof will appear, in reference to the appended diagrammatic drawing, representative, as non-restrictive examples, several possible embodiments of the tray which it relates to.

Figure 7:
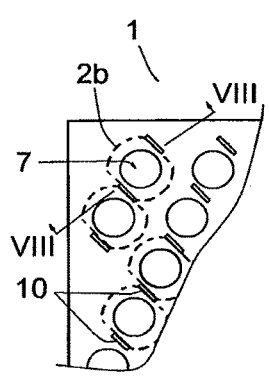
FIG. 7 is a partial top view of the tray according to another embodiment, the syringe bodies being shown in dashed lines.
Figure 8:
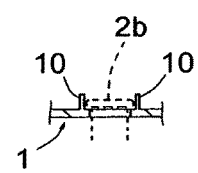
Figure 9:
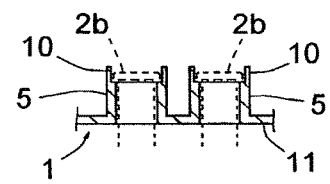
Figure 10:
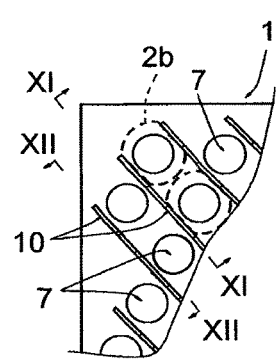
Figure 11:
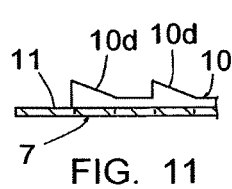
Figure 13:
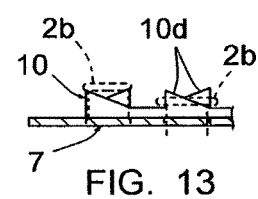
Figure 12:
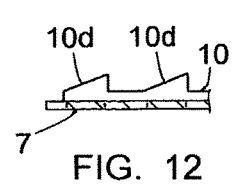
Figure 14:
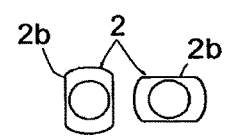
Figure 15:
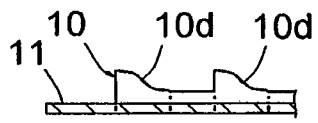
Figure 16:
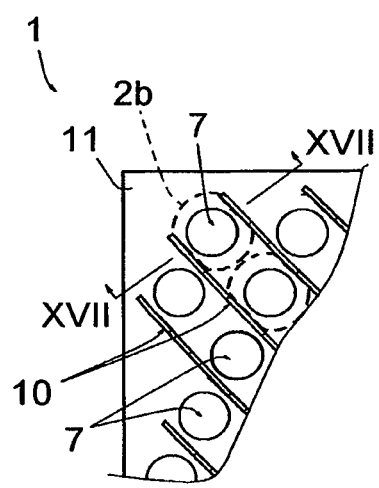
Figure 17:
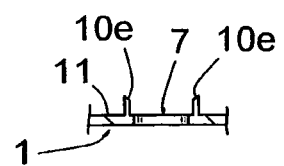

FIG. 8 of it is a cross-section according to the line VIII-VIII of FIG. 7;

FIG. 9 is a partial top view of the tray according to another embodiment;

FIG. 10 is a partial top view of the tray according to still another embodiment, the syringe bodies being shown in dashed lines;

FIG. 11 is a sectional view according to the line XI-XI of FIG. 10;

FIG. 12 is a sectional view according to the line XII-XII of FIG. 10;

FIG. 13 is a cross-section according to the line XI-XI of FIG. 10, showing two syringe bodies in dashed lines, the one on left side on the figure being in the course of installation on the tray and the one on the right side on the figure is installed on the tray;

FIG. 14 is a view of the two syringe bodies of FIG. 13 in the respective positions which they occupy on this FIG. 13;

FIG. 15 is a view of the tray similar to FIG. 11 according to another embodiment;

FIG. 16 is a view of the tray similar to FIG. 10 according to still another embodiment;

FIG. 17 of it is a view in section according to line XVII-XVII of FIG. 16; and

Figure 18:
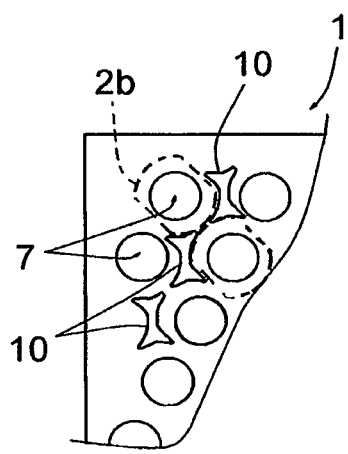

FIG. 18 is a view of the tray similar to FIG. 10 according to still another embodiment.

By simplification, the parts or elements of an embodiment which are found in an identical or similar way in another embodiment will be identified by the same numerical reference and will not be described again.

FIGS. 1 to 4 show a tray 1 for positioning syringes bodies 2 put in place in a packaging box 3 sealed by a membrane 4 and sterilized. This assembly is used to transport the syringe bodies 2 from one site to another, in particular from a site of manufacture of the syringe bodies 2 to a site of filling of these syringe bodies 2 and assembly of the syringes.

The syringe bodies 2 represented are well-known in themselves. Each one of them is made of glass or plastic or any suitable material, and includes a cylindrical barrel 2a and a proximal flange 2b integral therewith. The barrel 2a forms a delivery tip, equipped with a needle, this tip and this needle being covered by a protection cap 2c, yet in place on the syringe body 2 at this stage of manufacture. The flange 2b is of noncircular form, having thus a length and a width; it includes two rectilinear longitudinal edges 2b1 and two curved end edges 2b2 centred on the revolution axis of the body 2, like more particularly visible on FIG. 4. This flange 2b can receive for instance a part such as the one described in the document U.S. Pat. No. 5,667,495, forming bearing surfaces for a user's fingers at the time of the injection and forming a stop preventing the withdrawal of the piston of the syringe out of the barrel 2a.

The tray 1 includes, on a face, series of tubular walls 5, or "chimneys", grouped by rows 6, which form upper openings 7 and conduits intended to receive the syringe bodies 2. The latter are engaged in these conduits until their flanges 2b come to rest against the free edge of the chimneys 5 delimiting the openings 7. The inner diameters of said conduits are such that these conduits are able to receive the barrels 2a without substantial radial play but with possibility of free pivoting in the conduits.

Figure 1:
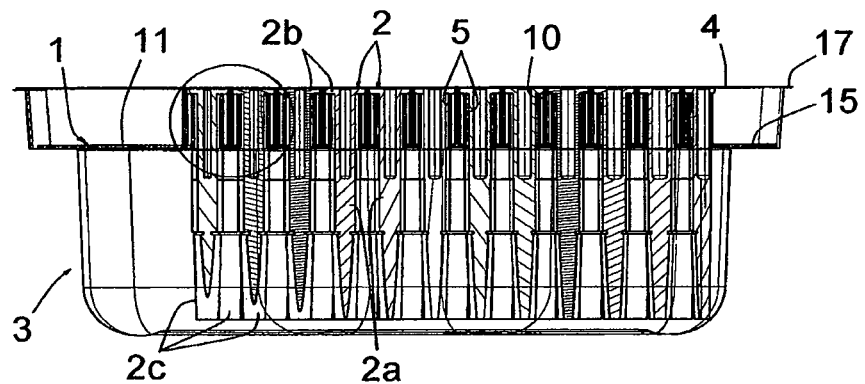
FIG. 1 is a side view, partially cut out, of a tray for positioning syringe bodies according to a first embodiment, this tray being placed in a sealed and sterilized packaging box.
Figure 2:
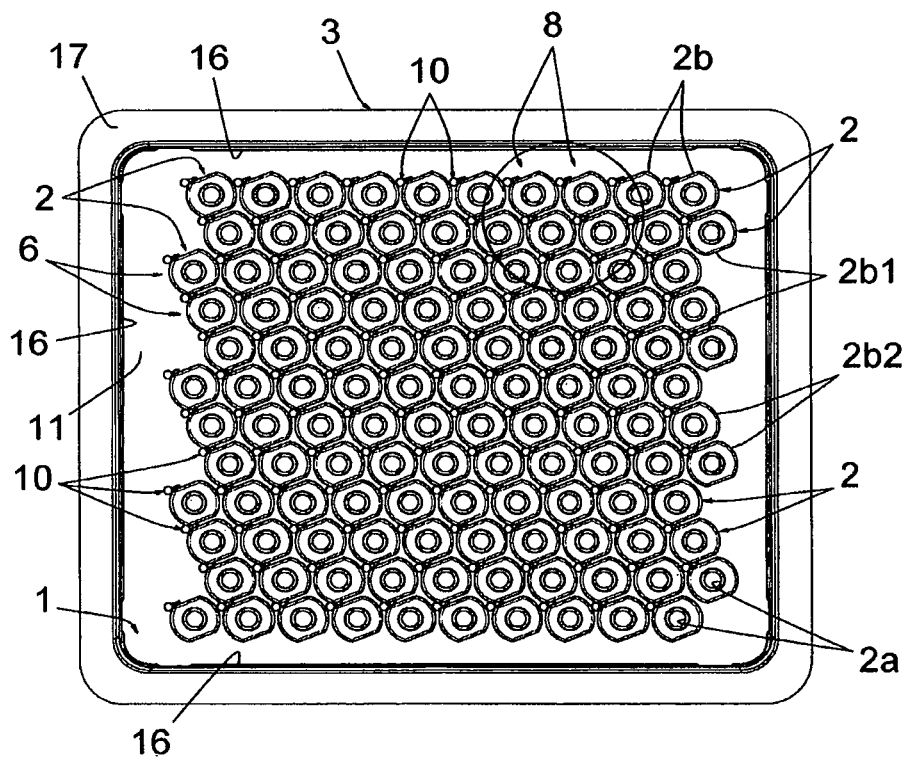
FIG. 2 is a top view of this tray.

It appears on FIG. 2 that chimneys 5 of a row 6 are offset in the longitudinal direction of this row compared to chimneys 5 of the adjacent rows 6 so that chimneys 5 of rows 6 form oblique rows 8 of syringe bodies 2. In the embodiment shown, these oblique rows 8 form angles of about 70° with the longitudinal directions of rows 6. It also appears that the chimneys 5 are arranged ones with respect to the others, within the same row 6 or the same row 8, and from a row 6 or row 8 to an adjacent row 6 or row 8, so that the rectilinear edges 2b1 and curved edges 2b2 come in the vicinity to each other when the syringe bodies 2 are inserted in the chimneys 5.

Figure 3:
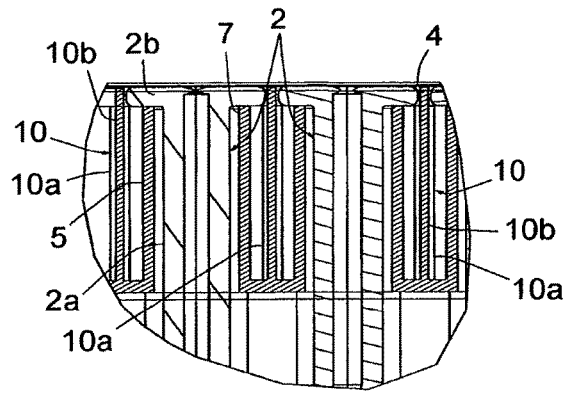
FIG. 3 is an enlarged scale view of the part surrounded by a circle on FIG. 1.

FIG. 3 also shows that the length of the chimneys 5 is such that the proximal surfaces of the flanges 2b, i.e. the surfaces of these flanges opposed to the barrels 2a, come just under the sealing membrane 4 of the box 3 when tray 1 is put in place in this box 3.

Figure 4:
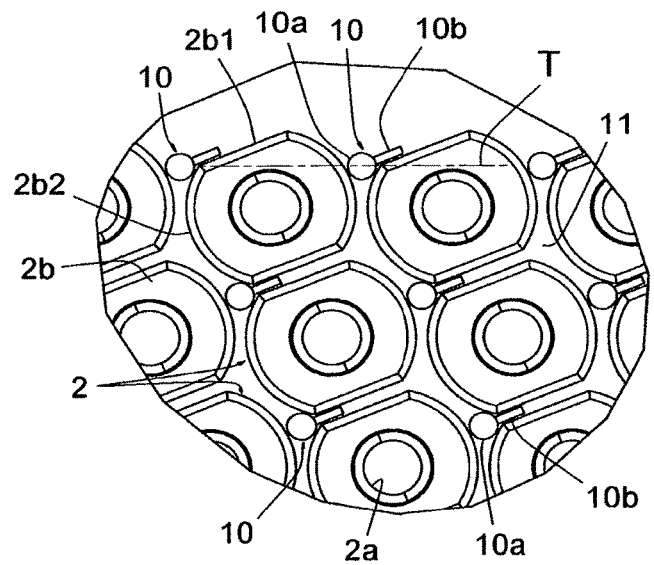
FIG. 4 is an enlarged scale view of the part surrounded by a circle on FIG. 2.

Tray 1 includes moreover, as it is more particularly shown in FIGS. 3 and 4, positioning projections 10 making it possible to place the flanges 2b in a determined angular position with respect to rows 6. Each projection 10 extends perpendicular to the plate 11 of the tray 1, and includes a cylindrical stem 10a and a wall 10b extending radially from this stem 10a, to which it is connected. The stem 10a is located substantially halfway of two consecutive chimneys 5 of the same row 6 and has its axis located substantially on a tangent T of the wall of these two chimneys 5 (see FIG. 4). Its diameter is such that the curved edges 2b2 of three flanges 2b of three adjacent syringe bodies 2 (two syringe bodies 2 located in the same row 6 and the syringe bodies 2 located in an adjacent row 6) come in the immediate vicinity from it when these syringe bodies 2 are in place in the chimneys 5. Its length is such that its free end extends up to the level of the proximal surfaces of the flanges 2b (see FIG. 3). The wall 10b extends according to a determined angle with respect to the row 6, according to the desired determined angular position of the flanges 2b on the tray 1, namely according to an angle of about 20° with respect to row 6 in the example shown. As that appears on FIGS. 3 and 4, the length of this wall 10b is such that it extends up to the membrane 4, being inserted between the rectilinear edges 2b1 of two flanges 2b placed in two adjacent rows 6.

Each row 6, at one of its ends (that appearing on the left on FIG. 2) includes a projection 10 identical to the other projections 10 of this row 6, placed in alignment with these other projections 10.

The box 3 forms a peripheral shoulder 15 on which the peripheral zones of the tray 1 come to rest when this tray is inserted in this box. The latter can also form snapping ribs 16 retaining these peripheral zones against this shoulder 15 when box 3 is turned upside down.

The membrane 4 is sealed on an outer edge 17 which the box 3 also includes. Apart from this edge 17, this membrane 4 rests on the projections 10.

In practice, the syringe bodies 2 are inserted on the tray 1 with engagement of the flanges 2b between the projections 10 and inducing the determined angular orientation of these flanges like shown on FIG. 2 and immobilization of the flanges 2b in this determined angular orientation. It is thus possible to arrange the chimneys 5 in close positions, such that the flanges 2b are arranged in the immediate vicinity one with each other, with imbrications, and thus to significantly increase the density of the syringe bodies 2 on the tray 1. A quite higher number of syringe bodies 2 can be inserted on a tray 1, while allowing the external dimensions of the tray 1 to remain identical to those of the existing trays. This conservation of these external dimensions is indeed necessary not to induce too important modifications of the automated treatment units for handling and/or filling the syringe bodies 2.

This increase in the density reduces the number of boxes 3 necessary for the conditioning and the transport of a given number of syringe bodies 2, and thus the costs of conditioning and transport of these syringe bodies 2.

Figure 5:
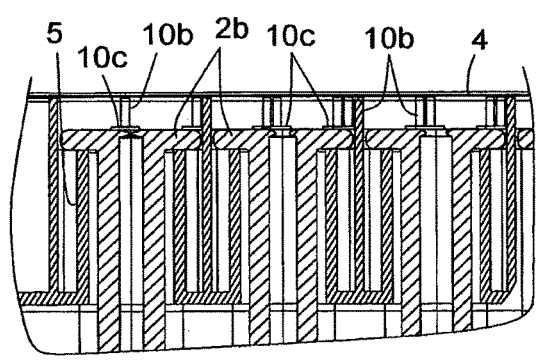
FIG. 5 is a view similar to FIG. 3 of the tray according to another embodiment.

FIG. 5 shows an embodiment in which the chimneys 5 have lengths less than those of the chimneys 5 of the embodiment shown on FIG. 3, so that the flanges 2b are remote from the membrane 4. The projections 10 include in this case snapping edges 10c, behind which the flanges 2b are retained when they are bearing against the free edges of the chimneys 5, and thus immobilized axially with respect to the tray. The determined angular orientations of the syringe bodies 2 are not thus likely to be lost when box 3 is turned upside down.

Figure 6:
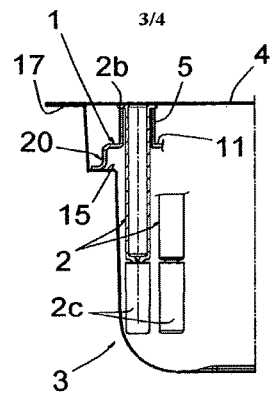
FIG. 6 is a side cut-out partial view of the tray according to another embodiment.

FIG. 6 shows an embodiment in which the chimneys 5 also have lengths smaller than those of the chimneys 5 of the embodiment shown on FIG. 3 but make it possible nevertheless to immediately place the flanges 2b under the membrane 4. Indeed, in this case, tray 1 includes a peripheral heightening base part 20 for heightening the plate 11 with respect to shoulder 15.

FIGS. 7 and 8 show a tray 1 deprived of the chimneys 5, in which the above mentioned projections are formed by walls 10 arranged on both sides of the openings 7 and oriented according to the desired determined angular position of the flanges 2b.

FIG. 9 shows a tray 1 with chimneys 5. Walls 10 are then arranged on the free ends of the chimneys 5, on two diametrically opposed sides of each one of these chimneys 5.

FIGS. 10 to 13 show a tray 1 deprived of the chimneys 5, in which the above mentioned projections are formed by rectilinear walls 10 arranged on both sides of the openings 7. These walls 10 are oriented according to the desired determined angular position of the flanges 2b and extend in a continuous way along rows 8 of openings 7. FIGS. 11 and 12 show that walls 10 including, in front of each opening 7, spaced tips forming rectilinear sloped edges 10d, the sloped edges 10d being located on two opposite sides of the same opening 7 and having reversed slopes. These edges form ramps which the flanges 2b meet during the insertion of the syringe bodies 2 in the openings 7 and against which these flanges slip further to this meeting. As shown on FIGS. 13 and 14, this slip makes it possible, when the syringe bodies 2 are engaged in the openings 7 with the flanges 2b in an angular position that does not corresponds to the desired determined angular orientation, to make these syringe bodies 2 pivot in these openings 7 until bringing the flanges 2b according to this desired determined angular orientation.

FIG. 15 shows an alternative in which the sloped edges 10d are curved and not rectilinear.

FIGS. 16 and 17 show a tray 1 deprived of the chimneys 5, in which the above mentioned projections are also formed by rectilinear walls 10 arranged on both sides of the openings 7, oriented according to the desired determined angular position of the flanges 2b and extending in a continuous way the rows 8 of openings 7. In this case, as it is visible on FIG. 17, walls 10 have bevelled free edges 10e, i.e. sloped according to the thickness of these walls, in the direction of the openings 7. In the same manner that previously described, the flanges 2b are meet these bevelled free edges 10e when the syringe bodies 2 are engaged in the openings 7 according to an angular position not corresponding to the desired determined angular orientation, the bevelled free edges 10e making it possible to make these syringe bodies 2 pivot in these openings 7 until bringing the flanges 2b according to said desired determined angular orientation.

FIG. 18 shows an embodiment in which the above mentioned projections are comprised of studs 10 having a form corresponding to that of the spaces existing between the flanges 2b of two adjacent rows of syringe bodies 2.

As appears from the preceding, the invention provides a tray for positioning elongated objects, in particular syringe bodies or syringes, having substantial advantages with respect to the trays of the prior art.

The invention was described above in reference to embodiments provided purely as examples. It goes without saying that it is not limited to these embodiments, but that it extends to all embodiments covered by the appended claims.

What is claimed is:

1. A tray for positioning elongated objects, each elongated object having a cylindrical body and a noncircular flange, the flange having a length greater than its width, the tray comprising:
a plate defining spaced apart openings arranged in parallel rows, the plate comprising a first row comprising a first plurality of spaced apart openings and a second row comprising a second plurality of spaced apart openings, each opening configured to receive the body of one of the elongated objects,
wherein the plate further comprises a plurality of projections extending therefrom, with each opening having at least one projection adjacent thereto, the at least one projection displaced from a perimeter of the opening such that the at least one projection contacts and positions a peripheral edge of the noncircular flange in a determined angular position when the elongated object is fully inserted into the opening, such that the flange of the elongated object inserted in the first plurality of spaced apart openings imbricates between two adjacent flanges of elongated objects inserted in the second plurality of spaced apart openings, and
wherein at least a portion of said projections include sloped edges forming ramps configured to cause the flanges to slide into the determined angular position when the elongated objects are inserted into the spaces.

2. The tray according to claim 1, wherein at least two projections are arranged on two diametrically opposed sides of at least one opening, and said at least two projections include edges of reversed slopes from one projection to the other.

3. The tray according to claim 1, wherein said sloped edges of the at least two projections are rectilinear.

4. The tray according to claim 1, wherein said sloped edges of the at least two projections exhibit a curved form.

5. The tray according to claim 1, wherein at least one projection exhibits beveled free edges.

6. The tray according to claim 1, wherein at least a portion of the projections are interrupted from the first row of openings to the second row of openings.

7. The tray according to claim 1, wherein at least a portion of the projections form a continuous ridge from the first row of openings to the second row of openings.

8. The tray according to claim 1, further comprising a plurality of chimneys delimiting at least a portion of the openings wherein at least a portion of the projections are arranged on the level of the free ends of the plurality of chimneys.

9. The tray according to claim 1, wherein at least a portion of said projections include retention means such that the flange of at least one of the elongated objects is releasably retained in the plate when the elongated object is inserted into at least one of the spaces.

10. The tray according to claim 1, further comprising at least one chimney delimiting at least one of the openings such that the flange of an elongated object inserted into the at least one opening rests thereon.

11. The tray according to claim 1, further comprising a heightening base part arranged on a bottom side of the tray proximate to a peripheral edge thereof.

12. The tray according to claim 1, wherein each opening has at least a second projection adjacent thereto, the at least a second projection displaced from the perimeter of the opening such that the at least a second projection contacts and positions a peripheral edge of the noncircular flange in the determined angular position when the elongated object is fully inserted into the opening.

* * * * *